United States Patent [19]
Schneider

[11] Patent Number: 5,167,144
[45] Date of Patent: Dec. 1, 1992

[54] METHOD AND APPARATUS FOR THE REMOTE MONITORING OF FLUIDS

[76] Inventor: Alfred Schneider, 5005 Hidden Branches Dr., Dunwoody, Ga. 30338

[21] Appl. No.: 591,966

[22] Filed: Oct. 2, 1990

[51] Int. Cl.⁵ .............................................. G01N 9/28
[52] U.S. Cl. ................................... 73/54.02; 73/439; 73/61.41; 73/64.52
[58] Field of Search ............... 73/61 R, 439, 438, 64.4

[56] References Cited

U.S. PATENT DOCUMENTS

| | | | |
|---|---|---|---|
| 3,765,227 | 10/1973 | Campbell et al. | 73/64.4 |
| 4,422,326 | 12/1983 | Sasaki | 73/439 X |
| 4,949,572 | 8/1990 | Wilen et al. | 73/439 X |

OTHER PUBLICATIONS (Hornyak and Weinberg, "Velocity of a Freely Rising Gas Bubble in a Soda–Lime Silicate Glass Melt", *Comm. Amer. Ceramic Soc.*, Nov. 1984: C244–C246).
(Jucha et al., "Bubble Rise in Glassmelts", *J. Amer. Ceramic Soc.*, 65:289–291 (1982)).
("Rising-Bubble Viscometers" in J. R. Van Wazer, et al., *Viscosity and Flow Measurement, A Laboratory Handbook of Rheology*, 282–287 Interscience Publishers, New York, (1963)).
(Shartsis and Spinner, "Viscosity and Density of Molten Optical Glasses", *J. Res. Nat'l Bureau Standards*, 46:176–194 (1951)).

*Primary Examiner*—Hezron E. Williams
*Assistant Examiner*—Joseph W. Roskos
*Attorney, Agent, or Firm*—Needle & Rosenberg

[57] ABSTRACT

The present invention provides a method and apparatus for measuring, particularly remotely, a first composition-dependent physical property, such as bubble rise velocity or dynamic viscosity, of a fluid comprising a container for holding the fluid at a certain level in order to form a surface on the fluid; a bubble delivery tube for introducing into the fluid at a first depth a first bubble having a first size; a vacuum pump for generating a carrier gas stream; a hood for capturing in the carrier gas stream the first bubble as it leaves the surface of the fluid; and detector in the path of travel of the carrier gas stream to detect the first bubble in order to determine the time of transit of the bubble from first depth to the surface of the fluid, so as to enable calculation of the average bubble rise velocity. In addition, a second bubble delivery tube for introducing a second bubble at a second depth can be added to allow calculation of the average bubble rise velocity independent of the position of the surface of the fluid. Addition of a temperature sensor and apparatus capable of monitoring a second composition-dependent physical property allow the determination of the composition of the fluid by reference to a ternary phase diagram.

35 Claims, 10 Drawing Sheets

METHOD AND APPARATUS FOR THE REMOTE MONITORING OF FLUIDS

BACKGROUND OF THE INVENTION

The present invention relates generally to the field of remote monitoring of fluids and, in particular, to a method and apparatus for the remote, near-continuous determination of the bubble rise velocity, viscosity, and other composition-dependent physical properties of a fluid. These physical properties, when correlated on a composition-dependent phase diagram for the fluid, can be used to ascertain the composition of the fluid. This invention has particular relevance to the remote monitoring of radioactive waste glasses.

The conversion of high-level liquid wastes arising from the reprocessing of spent nuclear fuels into a solid form is necessary to prevent the leakage of stored radioactive materials into the soil and to prepare the long-lived radioactive wastes for permanent disposal in geologic formations. Glass has been the preferred waste form because of its relative chemical stability, its capacity for incorporating various elements and compounds, and the existence of extensive experience with its production. Vitrification facilities for the conversion of high-level liquid wastes, primarily into borosilicate glass, have been in operation for several years and additional ones are in an advanced state of construction in many countries.

The properties of a glass are determined primarily by its composition, operating variables during its production, and the cooling rate after the glass is poured into a mold or canister. The chemical stability of a glass containing radioactive ingredients, as evidenced by a low leaching rate for most elements, is the property of paramount concern. Because variations in the chemical composition of the glass product may cause unacceptable variation in the leaching rates of certain radionuclides, great care is taken during the design of vitrification facilities to allow for very precise compounding of the ingredients and for continuous monitoring of sensitive operating variables. The high quality control standards in the production of the glass are part of the overall qualification process, which also includes monitoring the performance of the canisters, the transportation casks, and the geologic host repository.

However, it is recognized that regulatory authorities will require confirmatory test data, including the composition of the glass, when the glass is shipped to a repository. At present, the only way in which such a requirement could be met is to periodically remove glass samples, which are then chemically analyzed in a remotely operated analytical facility. Obtaining such samples is somewhat cumbersome because of the complexity of the remotely operated sampling equipment. The facilities for the transport and handling of the highly radioactive samples are equally complex and may require frequent maintenance. It is also possible that, because of the delays in obtaining the results of sample analyses, some canisters may be filled with glass that is outside the established specifications and the disposal of such material could pose problems. Sampling can only be done at finite intervals and some uncertainty concerning the quality of the glass produced between samplings would always remain.

Great strides have been made in recent years in the development of on-line control methods that are valuable not only in controlling various processes, but also in providing for the continuous monitoring of the quality of the product. The extension of such control methods to the production of radioactive waste glasses requires the availability of instruments that continuously provide an analysis of the glass product about to be poured into the canister. This is a formidable problem, considering the very high temperature of the molten glass, the intense radioactivity, and the complex composition of the glasses.

Thus, there exists a need for a method and apparatus for the near-continuous indication of the composition range, as well as deviations from a target product, for fluids such as radioactive glasses. Because it is possible to relate two or more composition-dependent physical properties of a fluid with its composition, an estimate of the composition of a specific type of glass can be determined from a measurement of the physical properties of the glass.

Most glasses, including radioactive waste glass forms, can be treated as ternary compounds. Triangular phase diagrams are frequently used to represent ternary systems or systems which can be simplified to pseudo-ternary. For instance, properties of borosilicate glasses can be shown on a ternary diagram in which $SiO_2$, $Na_2O$, and $B_2O_3$ are the constituent components. The waste glass from the Savannah River Plant can also be represented on a triangular phase diagram on which PHA (hydrolysis product from the cesium removal process), glass frit (having a specific composition), and sludge (precipitates formed during the neutralization of the high-level liquid wastes) are the primary constituents. Similarly, the glasses developed by the West Valley Demonstration Project can be treated as a pseudo-ternary system, with zeolite, sludge, and glass formers as the constituents.

Variation of the fluid's physical properties with composition can be represented on a triangular diagram as constant value lines for a given temperature (isopleths). By determining two physical properties at the same temperature, one can derive the composition of the fluid by locating the point where the two isopleths intersect. The location of the point of intersection is facilitated if the respective lines representing the two properties do not intersect at small angles.

A literature search of physical properties for borosilicate glasses reveals that melt viscosity varies appreciably with composition, the density changes only slightly, and the electrical resistivity is quite composition-dependent, but to a lesser extent than viscosity. Also, for this type of system, isopleth curves for viscosity/density and viscosity/electrical resistivity intersect at appreciable angles and thus, are appropriate variables for determining the composition. The density/electrical resistivity combination intersects at small angles and would consequently produce larger uncertainties in the derived composition values.

However, the selection of the physical properties used to determine the composition of the fluid must take into consideration the availability of suitable measuring methods and apparatus. For instance, viscosity is monitored to determine chain length during the polymerization of monomers to form polymers, which frequently occurs at high temperatures. In the case of radioactive waste glasses, it must be possible to measure these properties at temperatures above 1000° C., in an intense radiation field, and in contact with corrosive molten glass. In addition, the measuring techniques also have to be amenable to remote operational control at distances in excess of 15-20 feet.

While suitable methods are available for the determination of density and electrical resistivity under these conditions, no practical methods for the measurement of viscosity are known that could be adapted for use in these conditions. Although many methods are available for the measurement of the viscosity of liquids, the high temperatures at which measurements must be carried out with molten glass and the corrosiveness of the liquid have restricted the choices to the falling ball, flow rate through an orifice, and the rotating spindle methods. The latter method, generally consisting of a Brookfield type instrument adapted for high-temperature use, is the technique favored for the laboratory determination of the viscosity of molten glass samples. However, a Brookfield type viscometer cannot be adapted for the continuous monitoring of glass melts, especially for remote operation in an intense radioactive field. Other methods, such as the falling ball method or the measurement of flow rate through an orifice, would also be difficult to develop for fluids such as glass melts. Measurements requiring rotating instrumentation controlled electrically would be subject to degradation in the high radioactive field present in waste glass processing. Furthermore, methods requiring rotation of the fluid are less accurate for non-Newtonian fluids and falling ball methods require the retrieval of the ball. Thus, a novel approach to continuous or near-continuous remote measurement of the viscosity or other physical properties of a fluid is needed.

SUMMARY OF THE INVENTION

The above disadvantages of the prior art for remotely monitoring a fluid, particularly glass melt, are overcome by the present invention, which comprises a method and apparatus for the measurement, preferably from a remote location, of the average bubble rise velocity, the viscosity, and other composition-dependent properties of a fluid. In addition, the composition of the fluid can be estimated by determining the point of intersection of the isopleths for two or more of these composition-dependent properties.

In particular, a carefully sized bubble, preferably gas and most preferably helium, is introduced into the fluid, preferably a molten glass, at a known time from a bubble delivery tube located at a known depth in the fluid. The transit time for the bubble to rise to the surface of the fluid from this depth is determined by capturing the bubble as the bubble leaves the surface of the fluid in a carrier gas stream having a known flow rate, passing the carrier gas stream through a remote detector capable of sensing the bubble gas, and measuring the time at which the bubble gas is detected. From these measurements, the average rise velocity of a bubble in the fluid can be determined.

Alternatively, a second bubble can be introduced from a second bubble delivery tube located at a different known depth in the fluid followed by capture in the carrier gas and detection of the bubble gas similarly to the first bubble. This procedure allows for a calculation of the average rise velocity that does not require knowledge of the position of the surface of the fluid.

In addition, upon measurement of the density of the fluid, the dynamic viscosity of the fluid can be calculated. Furthermore, following measurement of at least one composition-dependent physical property of the fluid other than dynamic viscosity or bubble rise velocity and the fluid's temperature, the composition of the fluid can be determined by locating the point at which isopleths for the dynamic viscosity or bubble rise velocity and the other composition-dependent physical property intersect on a triangular phase diagram for the fluid.

The invention also provides methods to control the size of the gas bubble to deliver a desired mass of gas in a pulsatile fashion from the end of a delivery tube. These methods include, preferably, a metered mass method, which employs apparatus comprising a metering chamber enclosed by two valves for opening and closing the ends of the metering chamber sequentially.

The remote monitoring system of this invention can be configured to allow computer control of the system, including bubble generation, bubble detection and data acquisition. Furthermore, the data can be processed with a computer, including all the calculations relevant to determining bubble rise velocity, dynamic viscosity, density, and temperature, as well as the graphic display of processes associated with the launch and detection of the bubbles. In addition, the measurements can be repeated frequently to provide for near-continuous monitoring of the fluid.

Accordingly, one of the objectives of this invention is to provide a method and apparatus that allows the monitoring of the bubble rise velocity and the viscosity of a fluid, particularly from a remote location.

It is a further object of this invention to combine the monitoring of the bubble rise velocity or the viscosity of a fluid with simultaneous monitoring of at least one other composition-dependent physical property of the fluid, such as density, specific gravity or electrical resistivity, and the fluid's temperature, thus allowing the monitoring of the composition of the fluid.

It is a particular object of this invention to provide for the remote monitoring of the bubble rise velocity, viscosity, and composition of glasses, particularly radioactive waste glass.

It is a further object of this invention to provide an improved method and apparatus for generating gas bubbles in which the mass of gas delivered is controllable, the exact instance of bubble launch is known, and the components of the generating system that require adjustment or are subject to radiation damage are located at some distance from the fluid into which the bubbles are being launched. It is a further object to provide a bubble generating system that provides for excellent reproducibility of bubble properties from one bubble to the next, that can be adjusted to change the diameter of the bubbles, and that is adaptable to computer control and remote operation.

It is also an object of this invention to provide a monitoring system that can complete a measurement, involving the introduction of the bubble into the fluid and the detection of the bubbles launched from either one or both bubble delivery tubes, and estimate the composition of the fluid in less than one minute.

These and other objects and advantages of the present invention are apparent to a person skilled in the art from the following detailed description, which is not intended to be limiting.

DETAILED DESCRIPTION OF THE INVENTION

The present invention provides a novel method and apparatus for the measurement of the viscosity of a fluid based upon the rise velocity of a gas bubble in the fluid. The bubble rise velocity (BRV) of gas bubbles in a fluid has been shown to be a function of the densities and viscosities of the gas and the fluid, the diameter of the gas bubble, and the gravitational constant. Other factors, such as a change in size of the ascending bubble due to diffusion, chemical reaction, or expansion caused by changes in temperature and hydrostatic pressure, may also have effects, which can be minimized by proper selection of the gas and of the range over which measurements are made.

The gas bubble generator of this invention controls the mass of gas delivered as a bubble and is designed to minimize the variability between bubbles. The bubble size is determined by the mass of gas delivered and by the hydrostatic pressure at the point of launch. The bubble gas is chosen so as to allow the size of the bubble to be unaffected by intrinsic properties of the fluid, such as viscosity and surface tension. The bubble gas also should be inert, have a low solubility in the fluid, and be amenable to a remote method for determining the BRV. The invention provides for the measurement of the exact time the bubble is introduced into the liquid and allows adjustment of the bubble diameter so that the BRV in the particular fluid measured is sufficient to complete a measurement cycle in less than one minute. Furthermore, all components of the generating system that require adjustment or are subject to radiation damage are located at some distance from the liquid being tested. In addition, the arrival time of the gas bubble at the surface of the fluid is capable of being measured from a remote location.

Figure 1:
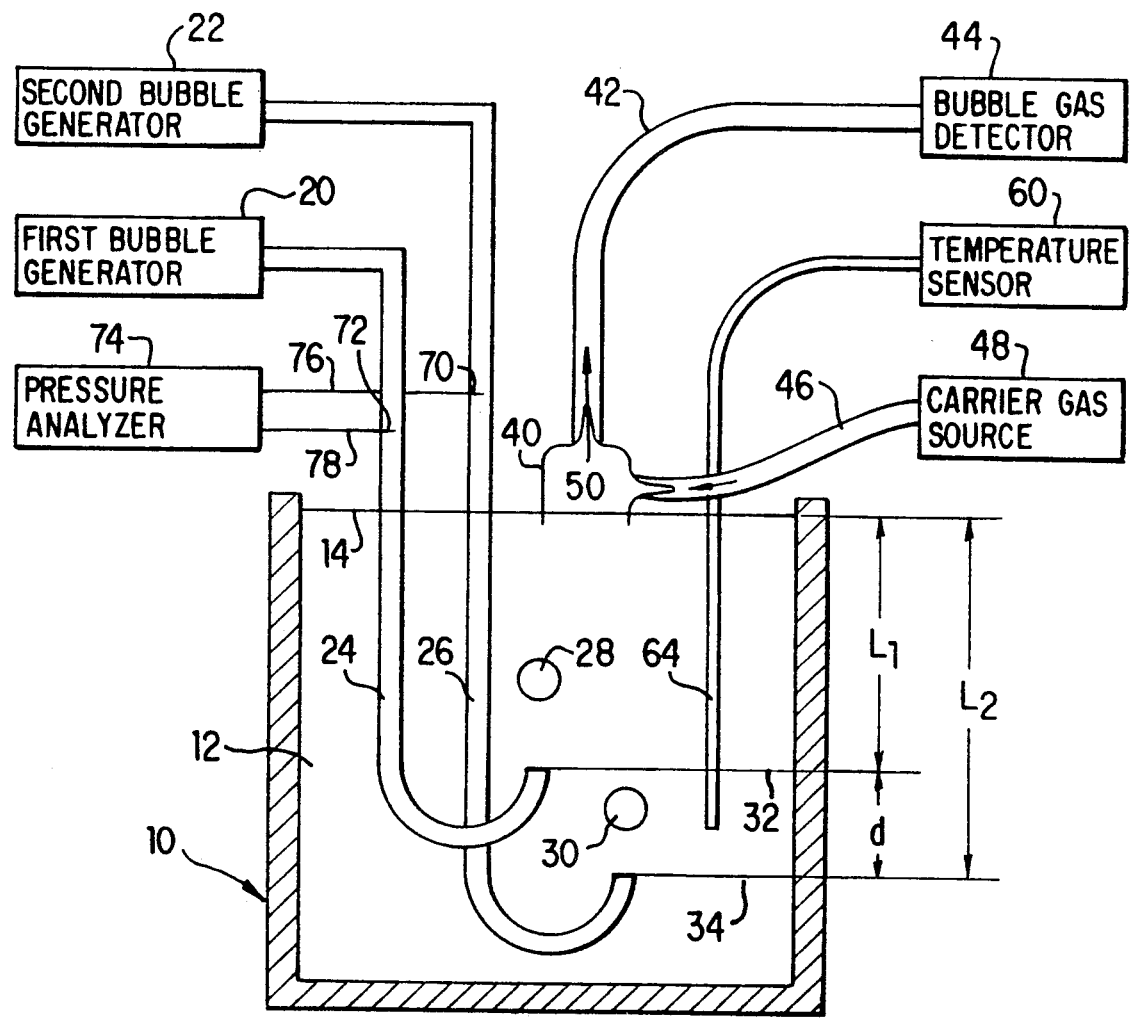
FIG. 1 is a schematic view of the apparatus utilized in measuring the bubble rise velocity of a fluid.

Referring to FIG. 1, a preferred embodiment of the apparatus for measuring the BRV in a fluid comprises a container 10 for holding a fluid 12 having a surface 14. A first bubble generator 20 is in flow communication with a first bubble delivery tube 24. A first bubble 28 is introduced into the fluid 12 by delivery tube 24 at a first depth 32 such that the distance between the fluid surface 14 and the first depth 32 is $L_1$.

The means for capturing and detecting the bubble 28 comprises a hood 40, which is positioned so as to capture the first bubble 28 as it leaves the surface of the fluid 14 in a carrier gas stream 50 that originates at the carrier gas source 48. The carrier gas steam 50, after exiting the source 48, passes through first conduit 46, hood 40, second conduit 42, and into bubble gas detector 44, such as a differential thermal conductivity cell, a mass spectrometer type leak detector or a helium detector.

Figure 2:
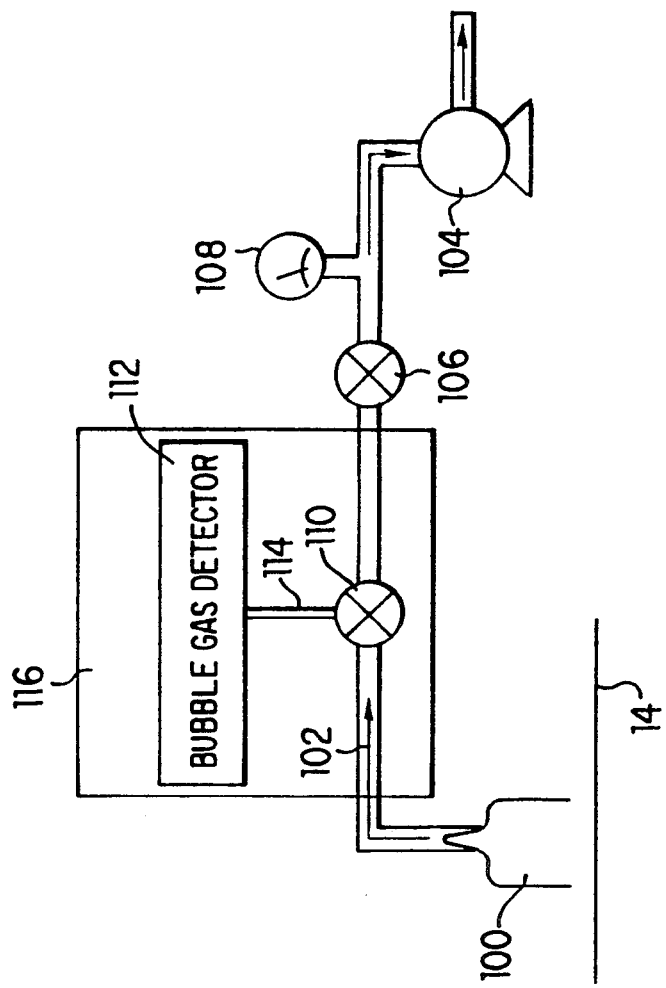
FIG. 2 is a schematic view of alternative preferred apparatus for capturing and detecting the bubble gas.

Referring now to FIG. 2, which shows alternative and preferable means for capturing and detecting the bubble 28, hood 100 is positioned above fluid surface 14 to capture the first bubble 28 in carrier gas stream 102, which is created by vacuum pump 104 that sucks ambient gas above the fluid's surface 14 into hood 100. It can be appreciated by one skilled in the art that ambient gas can enter hood 100 either by entering at the bottom of hood 100 immediately above fluid surface 14 as shown in FIG. 2 or by entering through an opening in hood 100, which can be slightly submerged in fluid 12 similar to hood 40 of FIG. 1. Intermediate the pump 104 and hood 100 is a bubble gas detector means 116 comprising a sampling valve 110 and bubble gas detector 112, preferably a helium detector, flowably connected by conduit 114. Intermediate the bubble gas detector means 116 and pump 104 are flow regulator valve 106 and flow meter 108. The abovementioned components comprise a first embodiment of the apparatus to measure the BRV of a fluid employing a single bubble generator.

Referring again to FIG. 1, a second embodiment for measuring the BRV of a fluid, which employs two bubble generators, is also shown. This embodiment has the added advantage over the single generator model in that measurement of the distance $L_1$ from the surface of the fluid 14 to first depth 32 is not necessary and thus, it is not necessary to know the position of the surface of fluid 14. This second embodiment comprises, in addition to the components present in the first embodiment, a second bubble generator 22, which is in flow communication with second bubble delivery tube 26. A second bubble 30 is introduced into the fluid 12 by delivery tube 26 at a second depth 34 such that the distance between fluid surface 14 and second depth 34 is $L_2$. Thus, the distance between second depth 34 and first depth 32 is given by d. Hood 40 is positioned such that it captures second bubble 30 as it leaves the surface of the fluid 14 in carrier gas stream 50, similar to the first bubble 28, with bubble gas detector 44 detecting first and second bubbles 28, 30.

Figure 3:
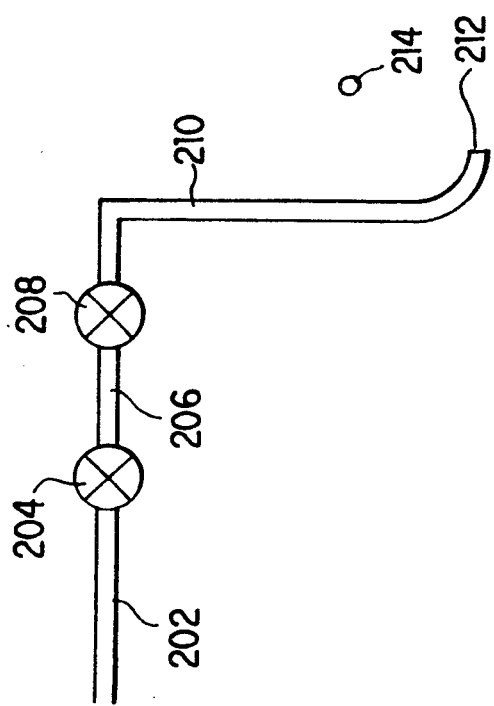
FIG. 3 is a schematic, detailed view of the preferred bubble generation apparatus.

A detailed view of either the first or second bubble delivery tube 24 or 26, respectively, is shown in FIG. 3. The bubble gas, preferably helium, from first or second bubble generator 20 or 22, respectively, enters conduit 202 and exits at bubble delivery tube tip 212, forming bubble 214. Intermediate tip 212 and conduit 202 along the path of travel of the gas is metering chamber 206. Chamber 206 is in flow communication with first valve 208, which regulates the flow of the gas between the chamber 206 and the tip 212, and second valve 204, which regulates the flow of the gas flowing into chamber 206. Valves 204, 208 are preferably fast-acting solenoid valves. Conduit 210, intermediate tip 212 and valve 208, is shaped to minimize bubble imperfections such as U-shaped or, preferably, L-shaped as shown in FIG. 3.

The bubble gas, preferably helium, is introduced into metering chamber 206 at an appropriate pressure, preferably 8 to 15 psig, by opening valve 204 while valve 208 remains closed. Valve 204 is then closed and valve 208 is opened to deliver a mass of gas determined by the difference between the pressures upstream from valve 204 and downstream from valve 208. If liquid is present in the tube, it is gradually expelled by successive pulses; the downstream pressure increases until gas bubbles are actually released into the liquid. Subsequently, every cycle produces a bubble 214, which is introduced into the fluid a brief instance after the opening of the downstream valve 208. The rapid pulse is brought about by the much higher pressure of the bubble gas in chamber 206 and the momentum imparted by the rapid expansion of the gas causes the bubble to be ejected like a projectile. Under these circumstances, the properties of the liquid (viscosity and surface tension) have a much smaller effect on the bubble launch mechanism. The variability of bubble rise velocities at different temperatures ranges from 1.4 to 3.2%.

Referring again to FIG. 1, temperature sensing means 64, which is electrically connected to temperature sensor 60, can be included in the apparatus to measure the temperature of fluid 12. Furthermore, means to monitor a second composition-dependent physical property of fluid 12, such as density or electrical resistivity, can be included in the apparatus to allow calculation of the composition of fluid 12. It can be appreciated by one skilled in the art that these measurements of a second composition-dependent physical property can be performed in many ways. However, because the density for fluid 12 can be calculated from pressure measurements at two different fluid depths, density is preferably measured by sensing the gas pressure in delivery tubes 24 and 26 using pressure transducers 70 and 72 as shown in FIG. 1. Signals from pressure transducers 70 and 72 are communicated to pressure analyzing means 74 via electrical wires 76 and 78, respectively, to determine the differential pressure.

Preferably, pressure transducers 70 and 72 are included in the apparatus to also sense the gas pressure in delivery tubes 24 and 26, respectively, before and after valve 208 is opened to allow determination of the mass of the gas in first bubble 28 and second bubble 30, respectively. In addition, the monitoring of these pressure measurements for a time after valve 208 is opened provides accurate measurement of the time that either first bubble 28 or second bubble 30 is introduced into fluid 12.

BUBBLE RISE VELOCITY (BRV) METHOD

Evaluation of the suitability of the bubble rise velocity viscometry of this invention required a comparison with viscosity data obtained using a standard method. Two liquids, CP grade glycerol and Cannon S-2000 Standard oil, were used to simulate molten glass. A data base was developed for the viscosities of these liquids using a set of seven certified Cannon-Fenske viscometers, which covered a range of kinematic viscosities from 3 to 100,000 centistokes and was obtained from Cannon Instruments Co., State College, PA. The viscometers were furnished with Certificates of Calibration that gave the viscometer constants at 40° and 100° C. Constants for other temperatures were obtained by interpolation. An agitated oil bath, provided with electric heaters and cold water coils, allowed temperature control to ±0.1° C. Excellent agreements were obtained by determining the viscosities of standard oils provided by Cannon Instrument Co.

The viscosities of both liquids were determined at temperatures ranging from 10° to 60° C. and covering a viscosity range between 291 and 15,075 centipoise. The data obtained generally agreed to within 5% with the corresponding data in the literature or with the supplier's certifications. Work with glycerol was discontinued when it was found that its hygroscopicity led to rapid absorption of water which sharply affected the viscosity. The kinematic viscosity (in centistokes), as determined with the Cannon-Fenske viscometers, was converted to the dynamic viscosity (in centipoise), by multiplying the former by the corresponding density.

Helium BRVs were determined visually using the apparatus of this invention at several temperatures for S-2000 oil. Fast-acting solenoid valves 204 and 208 of FIG. 3 were obtained from Angar Scientific. Flexible hoses and Swagelock fittings were used to connect the metering manifold of FIG. 3 with delivery tubes 24 and 26. The delivery tubes 24 and 26 were made of glass, copper, or Inconel. Pump 104 of FIG. 2 consisted of an Emerson air pump.

Quantitative relations for small bubbles were shown to agree with the Stokes or with the Hadamard-Rybczynski formula, which are similar, except for a constant of $\frac{1}{3}$ in the former and 2/9 in the latter. As shown in Table 1, dynamic viscosities based on BRVs and calculated by the Hadamard-Rybczynski formula are generally lower than the corresponding viscosities obtained with the Cannon-Fenske viscometer (CF). This suggests that as more experimental data are obtained, an empirically derived relation will be slightly different than either of the above formulae. Because of this uncertainty, a comparison of the BRV and CF viscosity measurements was made by calculating reduced reciprocal velocities (=velocity at 25° C. divided by the velocity at a given temperature) and reduced CF dynamic viscosities (=viscosity at a given temperature divided by the viscosity at 25° C.). These results are shown in Table 2.

TABLE 1

| | BRV and CF Viscosities of Cannon S-2000 Oil | | | |
|---|---|---|---|---|
| Temp (°C.) | BRV (cm/sec) | BRV Viscosity (poise) | CF Viscosity (poise) | Difference (%) |
| 22.5 | 1.14 | 70.83 | 68.00 | −4.2 |
| 26.0 | 1.78 | 45.01 | 49.50 | −9.1 |
| 33.0 | 3.22 | 24.90 | 26.80 | −7.1 |
| 40.0 | 6.00 | 13.23 | 15.80 | −16.2 |

TABLE 2

| | Comparison of Reduced Reciprocal BRVs and Reduced (CF) Viscosities | | | |
|---|---|---|---|---|
| Temp (°C.) | BRV (cm/sec) | (BRV)25/(BRV) | (CF)$\eta t/\eta 25$ | Difference % |
| 22.5 | 1.14 | 1.40 | 1.25 | +12 |
| 25.0 | 1.60 | 1.00 | 1.00 | 0 |
| 26.0 | 1.78 | 0.90 | 0.90 | 0 |
| 33.0 | 3.22 | 0.50 | 0.49 | +2 |
| 40.0 | 6.00 | 0.27 | 0.28 | −4 |

Bubble diameters, as estimated from photographs, ranged from 0.76 to 1.65 cm. As expected, the diameter was found to be a linear function of the cube root of the difference of the pressures upstream valve 204 and downstream valve 208. Correlation of the data by the least square method gave the following equation:

$$D_B = \sqrt[3]{(P - 0.133)} + 0.1689,$$

where $D_B$=bubble diameter, cm and P=He pressure upstream valve 204, psig

It was found that the shape of the delivery tube was very important. Tubes which are turned upwards (U-shaped, 180°) were found to contain residual liquid, which periodically resulted in a malformed bubble caused by entrapped liquid. This situation was remedied by using a tube with a 90° bend (L-shaped), which gives a slightly curved initial bubble trajectory but which prevents the trapping of liquid in the tube, as shown in FIG. 3. The preferred version of the delivery tube was vertical with a very short bend and an aperture located as low as feasible.

It was observed during the studies using the oil that the bubble is actually introduced into the liquid a very short time period after closure of valve 208. The visual observations were compared with the pressures obtained from monitoring the pressures upstream valve 204 and downstream 208 so that pressure changes with time could be used for diagnostic purposes.

For molten glass, the initial bubble launch sequences are similar, but a substantial difference was noticed involving the bubble release time. After a bubble is introduced into the melt, capillary action tends to draw a small amount of liquid into the tube creating a plug. In subsequent cycles, bubbles are released after the plug is breached (about one second after valve 208 is opened). This delay appears to be advantageous because it facilitates monitoring of the pressure within the delivery tube and thus precisely determines the time at which a bubble is released.

During the development of a system for the generation of helium bubbles, it became necessary to have a technique for assessing the degree to which bubble sizes could be controlled. From the equations which have been found to represent satisfactorily the rise velocity of gas bubbles in liquids, it was evident that if the viscosity and specific gravity of the liquid are kept constant, which would be the case if the temperature is carefully controlled, the rise velocity is proportional to the square of the bubble diameter. Thus, the degree of size uniformity can be determined from the distribution of rise velocities in the same liquid at constant temperature.

Bubble shapes and diameters were determined photographically with a Nikon 8008 camera. In general, the bubbles were approximately spherical in shape, with a pear shape being noticed immediately after launch. The rise velocity measurements were made visually by timing the interval between the rise of the bubble past two index lines. This method was not very precise, because at lower viscosities the time intervals were on the order of only one second. Multiple exposure photography, using the precision timer of the Nikon camera, was also used to estimate the rise velocity. The volume for the chamber 206 was determined by introducing bubbles into an inverted burette filled with water. The calculations of the chamber 206 volume were made with the ideal gas law equation, taking into account variations in atmospheric pressure and ambient temperature. These results were adequate for basing all subsequent bubble volume (or diameter) estimates on the supply gas and hydrostatic pressures.

However, it was also found that the means for capturing and detecting the helium gas bubble of this invention was also useful in estimating the mass of helium in the bubble. The accurate dispensing of a desired mass of helium contained in chamber 206 requires precise measurements of the gas pressure in chamber 206. These measurements were accomplished with a high-precision OMEGA manometer. For computer data acquistion, in-line pressures were obtained with transducers, such as transducers 70 and 72 of FIG. 1. Following calibration of the transducers, the analog output from the transducers was fed into an OMEGA WB-AAI-B high-resolution data acquisition card. The analog signals were converted to digital outputs with 16 bit resolution at speeds of 200-225 samples per second and fed into an IBM-compatible PC via a serial port. The software provided for the OMEGA card permitted a continuous display of the line pressures as a function of time.

Figure 4:
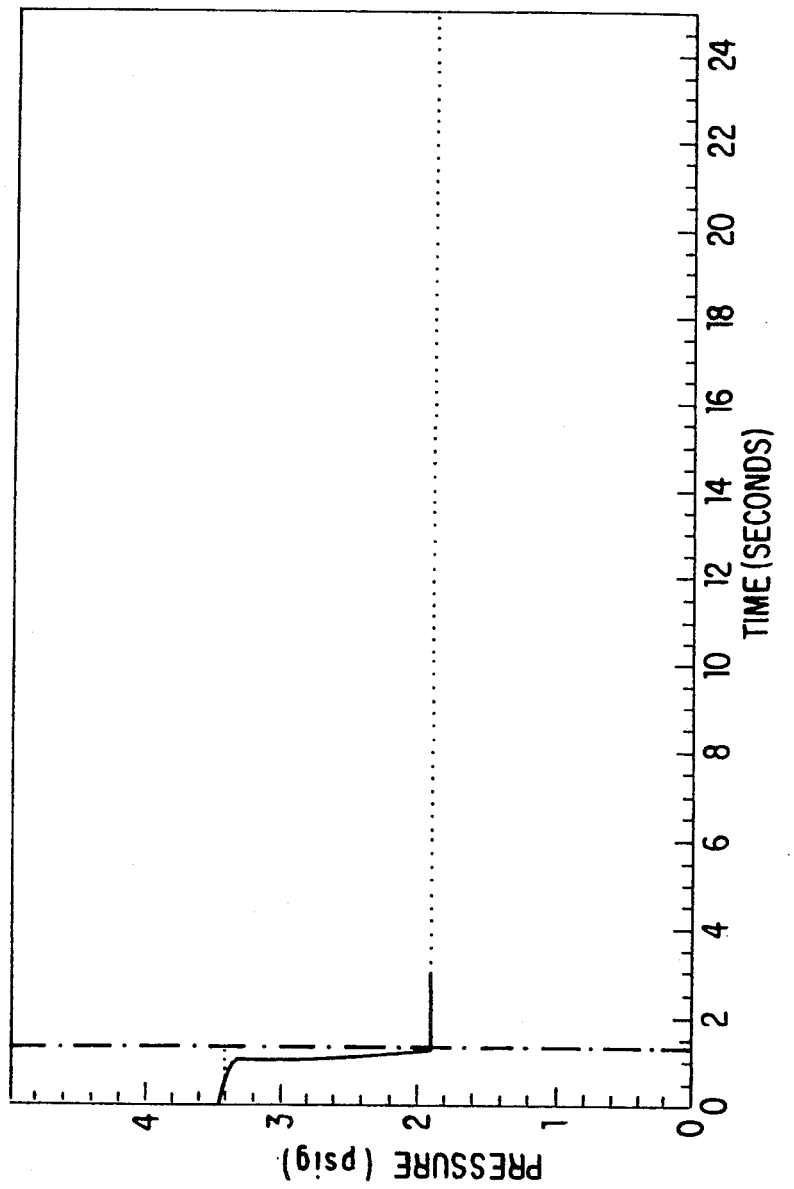
FIG. 4 profiles the pressure in a delivery tube during a normal introduction of a bubble into the fluid.

FIG. 4 shows the pressure in the delivery tube 210 of FIG. 3 after closure of valve 208 during introduction of a helium bubble into molten glass. The delay of about one second caused by the presence of a molten glass plug is clearly visible. The upper pressure plateau corresponds to the pressure in tube 210 and chamber 206 (because valve 208 is open). The lower plateau corresponds to the hydrostatic pressure at the point in the liquid at which the bubble is introduced. The helium mass of the bubble can be calculated from the volume of chamber 206, ambient temperature, gas pressure before valve 208 is opened, and line pressure in tube 210 after valve 208 is opened.

The mass of the gas bubble can also be calculated from the two pressure plateaus described above. This pressure difference is, however, considerably smaller and the bubble mass estimate will be less accurate. The ability to continuously monitor and record the line pressures before and after the launch of the gas bubble provided an excellent means to verify the constancy of bubble mass over a period of several days during which hundreds of bubbles were launched.

Monitoring the pressure profile also provided a useful diagnostic tool. A small leak in the system causes the absence of the higher plateau and the pressure decays to the lower plateau somewhat slower. Furthermore, the introduction of two, rather than one, bubbles can be detected from a bubble gas level profile.

To control the temperature during the studies involving glass melts, a Lindberg Model No. 56622 High Temperature crucible furnace and a Eurotherm 818 communicating temperature controller were used. Control of the temperature of the molten glass, using Inconel-sheathed D-type thermocouples, was possible to ±1° C. All internal metal tubes (bubble delivery tubes and thermocouple tubes) were Inconel. Alumina crucibles obtained from Coors, Golden, Colorado were used in most of the experiments. The alumina and Inconel showed little evidence of corrosion by the molten glass, except at the liquid-air interface where severe attack occurred.

A major challenge overcome by this invention was the development of a remote method for the measurement of BRV. The approach pursued consisted of determining the exact arrival time of a helium bubble at the liquid-gas interface using a gas detector, such as a helium detector. Several types of gas detectors are suitable for this purpose: the differential thermal conductivity cell and the mass spectrometer type leak detector are two widely used instruments. A Varian Leak Detector, Model 936-40 portable helium leak detector was used in the following studies. A sampling valve 110 (FIG. 2) with micrometer adjustment allowed the withdrawal of a small gas sample from the carrier line containing the helium spike. Initially, the sampling valve plugged up frequently by volatile glass components. A porous metal filter installed in the carrier line remedied this problem. The leak detector provided visual, audio, and analog electrical signal outputs. The latter was used with the computerized data acquisition system.

As discussed above and shown in FIG. 1, the helium bubble emerging from the fluid is captured in hood 40, which in the embodiment of FIG. 1, is partially immersed in the fluid. A nitrogen carrier stream is introduced into hood 40 via conduit 46 to flush the helium into a transfer conduit 42, which is connected to the helium detector 44 located at a distance of several feet. The arrival of the helium spike is signaled by helium detector 44 as an increase in output voltage, which is proportional to the helium concentration in the nitrogen carrier. By carefully controlling the flow rate of the carrier gas, and thus the travel time of the helium spike between hood 40 and detector 44, it is possible to calculate the exact arrival time of the bubble at the liquid-gas interface.

The BRV measurement is further simplified by employing two delivery tubes, which introduce helium bubbles of nearly equal mass but at different depths. Because the spacing of the first and second depths 32 and 34 are known and the difference between the total time elapsed from the introduction to the detection of the two helium bubbles is measured, the average rise velocity between the two levels can be calculated by dividing the time difference by the level difference.

As shown in FIG. 2, the location of hood 100 and carrier gas introduction can be preferably modified to prevent depressing the fluid 12 by excessive pressurization. The bottom of hood 100 is kept out of the liquid and air carrier gas is transported to detector 112 by suction produced with a metering pump 104.

The calculational procedure with reference to FIG. 1 is as follows:

r = average radius of bubbles 1 and 2 (controlled by bubble generators)

$t_1$ = time for bubble 1 to traverse distance $L_1$ (measured)

$t_2$ = time for bubble 2 to traverse distance $L_2$ (measured)

d = difference between levels of bubble launch (known)

$L_1$ = vertical distance of bubble 1 launch point from liquid-gas interface (varies with liquid level)

$L_2$ = vertical distance of bubble 2 launch point from liquid-gas interface (varies with liquid level)

$\Delta P$ = differential hydrostatic pressure between bubble launch points (measured)

t = time for bubble 2 to traverse distance d (calculated)

General Relation (simplified):

$$\eta = \frac{k\rho g r^2}{v}$$

where v = average rise velocity of bubbles 1 and 2 (calculated)

$\eta$ = viscosity of liquid (calculated)

p = specific gravity of liquid (calculated)

g = gravitational constant (known)

k = 2/9 in Stoke's formula or k = ⅓ in Hadamard-Rybczynski formula.

But t = $t_2 - t_1$ v = $d/t_2 - t_1$ p = $\Delta P/gd$ so $$\eta = k\left(\frac{\Delta P}{gd}\right)gr^2 / \frac{d}{t_2 - t_1} = k(\Delta P)r^2(t_2 - t_1)/d^2$$

In the absence of factors which delay the prompt "bursting" of the bubble at the liquid-air interface, the remote bubble detection method based on a gas, preferably helium, spike in a carrier gas worked very well. However, when the fluid exhibited high surface tension or when a crust or solid materials were present on the fluid surface, irregular delays were encountered before the bubbles burst and this introduced appreciable errors.

A NCR PC/AT compatible computer was used to monitor and control the apparatus of this invention. This computer contained a switchable 6/10 MHz 80286 processor, 640 KBytes main memory and 512 KBytes expanded memory. Magnetic storage was provided by a 40 MByte Seagate disc drive partitioned into a 15 MByte disc, exclusively for laboratory software. Signal acquisition and experiment control was provided by an OMEGA WB-AAI-B high-resolution data acquisition card, which provides 16 analog-to-digital channels and 8 digital input/output channels. Serial and parallel ports provided communication with the furnace controller and a printer. Display was provided by a VEGA VGA card and an NEC high-resolution color monitor. This instrumentation provided moderate speed with excellent display and proved adequate for the apparatus.

The following outlines a bubble generation and detection sequence, employing helium gas. Immediately after starting the timer, a digital output channel is turned on energizing the SPDT relay, which controls the helium flow valves 204 and 208 of FIG. 3. When the relay is energized, valve 204 closes and valve 208 opens, injecting a mass of helium into the bubble delivery tube 210 at a constant preset pressure. After a brief time interval, the digital output channel is turned off, de-energizing the relay, which causes the valve 204 and 208 to reset. The helium bubble is ejected after a very brief time interval.

The arrival of the helium spike in the carrier gas at helium detector 112 of FIG. 2 is indicated by an increase in the detector output voltage, which is transmitted to the computer. A 100-point running average is calculated to eliminate false signals due to noise spikes. When a rise in helium concentration of 5% above the running average is detected, the timer is read and the total time elapsed between ejection of the bubble and detection of the helium spike is recorded. The bubble rise time is then calculated by subtracting from the total time the previously determined delay caused by bubble breakage and transport of the helium from the hood 100 to the detector 112.

The frequency at which bubbles can be launched into the fluid is determined by the total time elapsed between energizing the relay and detection of the helium. For the experiments reported herein, one bubble can be introduced into the fluid about every thirty seconds.

During a determination, simultaneously with the continuous acquisition and storage of data, a graphic display is provided, which provides continuous evidence of proper sequencing and performance of the helium bubble generation and detection. The length of the upper plateau, as discussed above, is an indication of the proper release of the bubble. The difference in the pressures of the upper and lower plateaus is a measure of the bubble size. The deviation of the time interval between the beginning of the lower plateau (i.e., time of bubble ejection) and beginning of the increase of helium concentration at the leak detector is an indication that the transport of the helium from the surface of the fluid to the detector proceeded normally. The shape of the helium leak detector output is an indication that only a single bubble was ejected. Finally, integration of the detector output signal provides an independent measure of the size of the bubble.

Under laboratory conditions where the surface of the fluid (i.e., the level of glass melt in a crucible) can be determined accurately, the BRV can be determined with a single bubble delivery tube. However, in an actual glass melter where the glass level varies, the BRV is best determined by using two bubble delivery tubes located at different depths.

Figure 5:
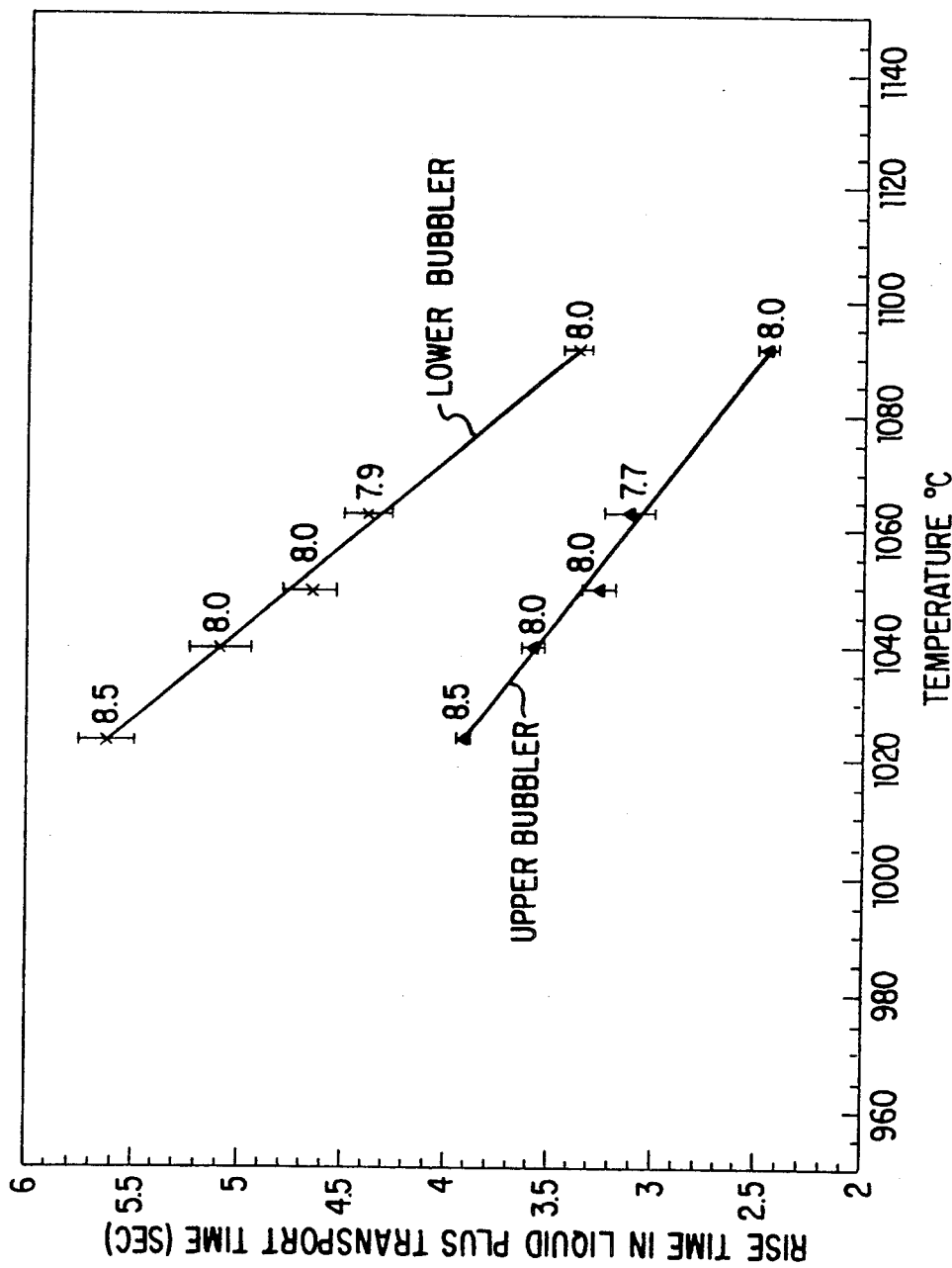
FIG. 5 shows the gas traveling times in glass melt as a function of temperature.
Figure 6:
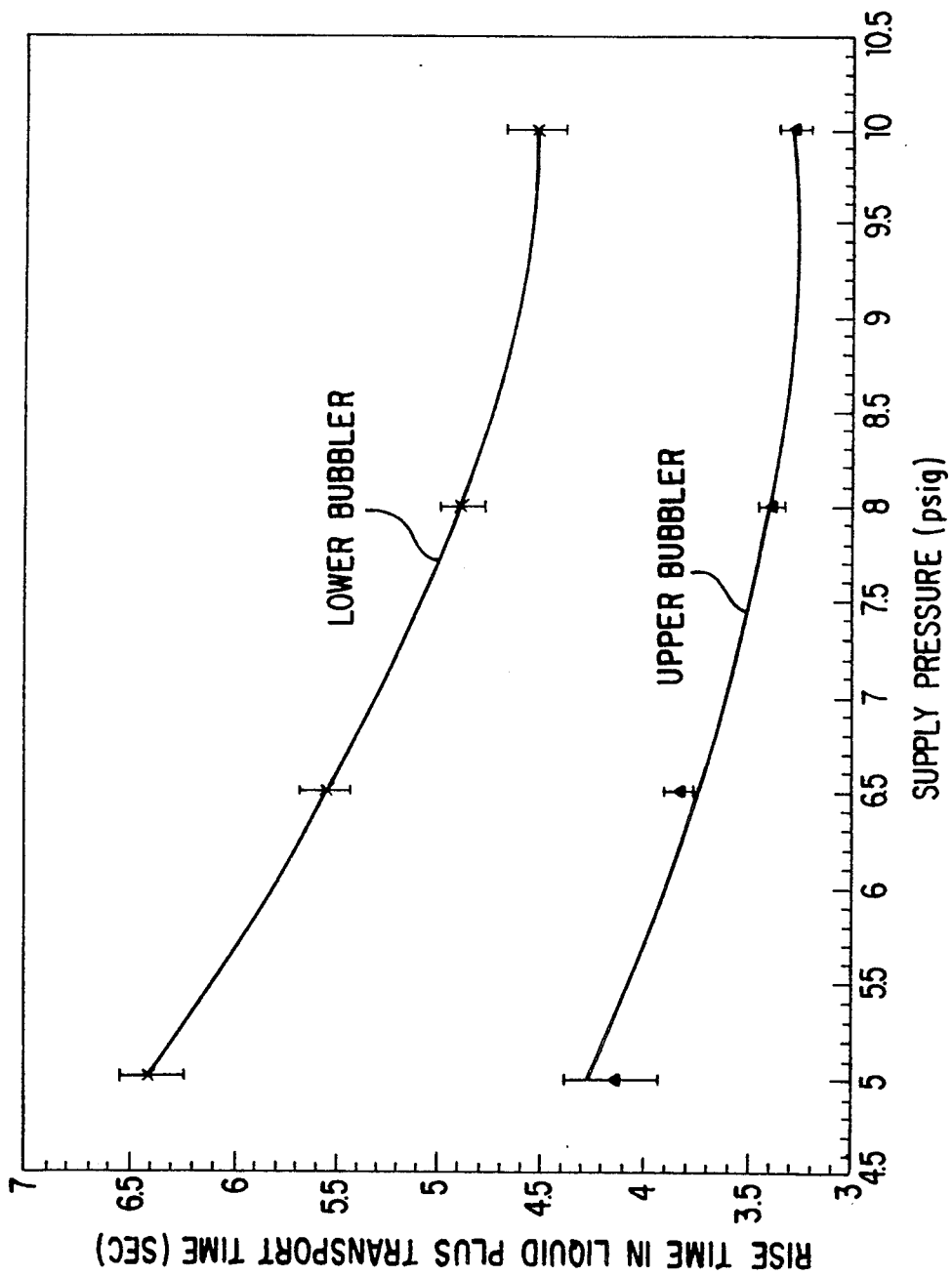
FIG. 6 shows the gas traveling times in glass melt as a function of supply pressure.

FIG. 5 shows that at a constant supply pressure, the gas traveling time for a helium bubble in glass melt decreases with rising temperature, in accordance with the expected decrease in the viscosity of the fluid. FIG. 6 shows that the gas traveling time at a constant temperature decreases with a rise in supply pressure (i.e., with increasing bubble size) as would be expected from Stokes' equation.

Figure 7:
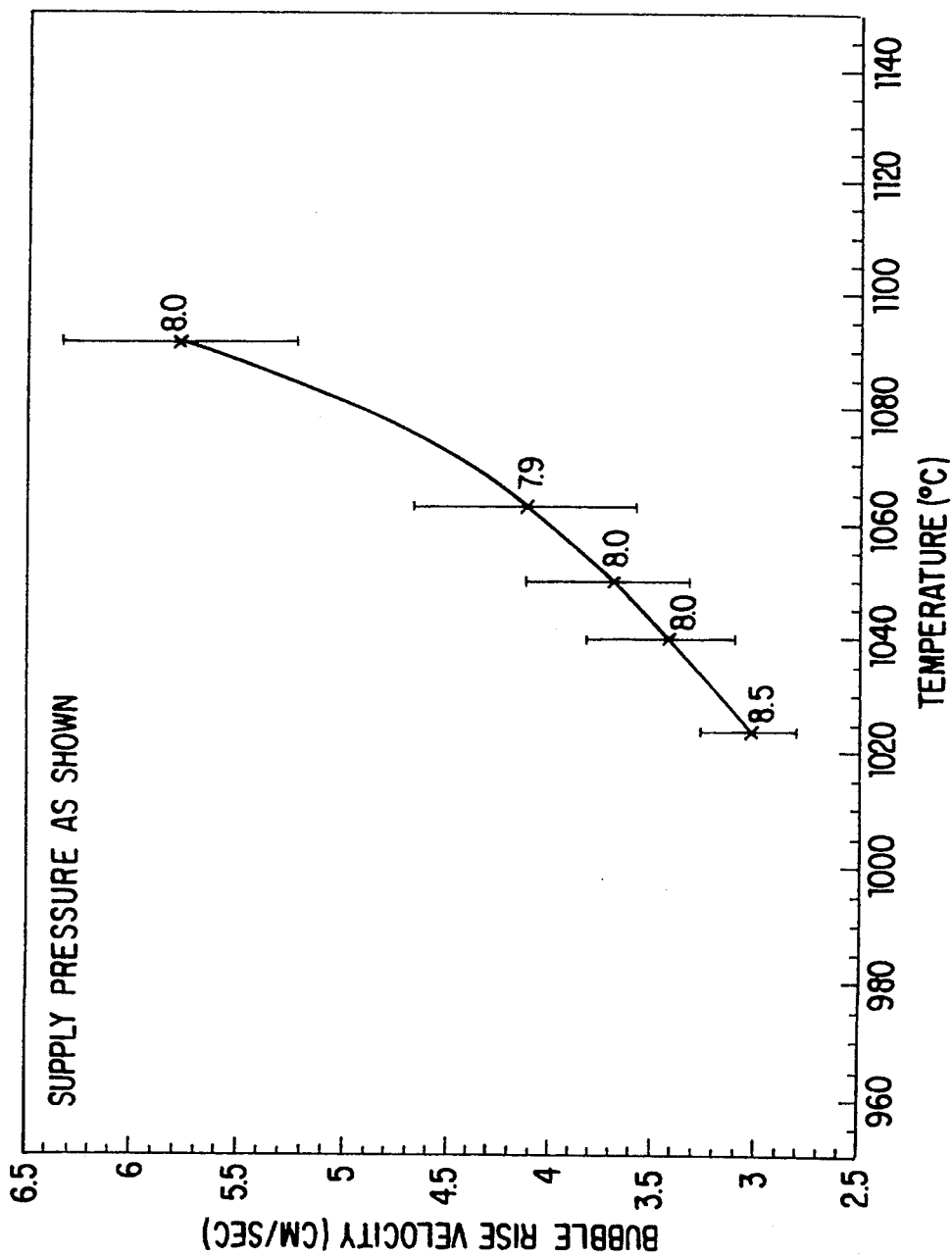
FIG. 7 shows the BRV as a function of temperature for Savannah River Laboratory waste glass.
Figure 8:
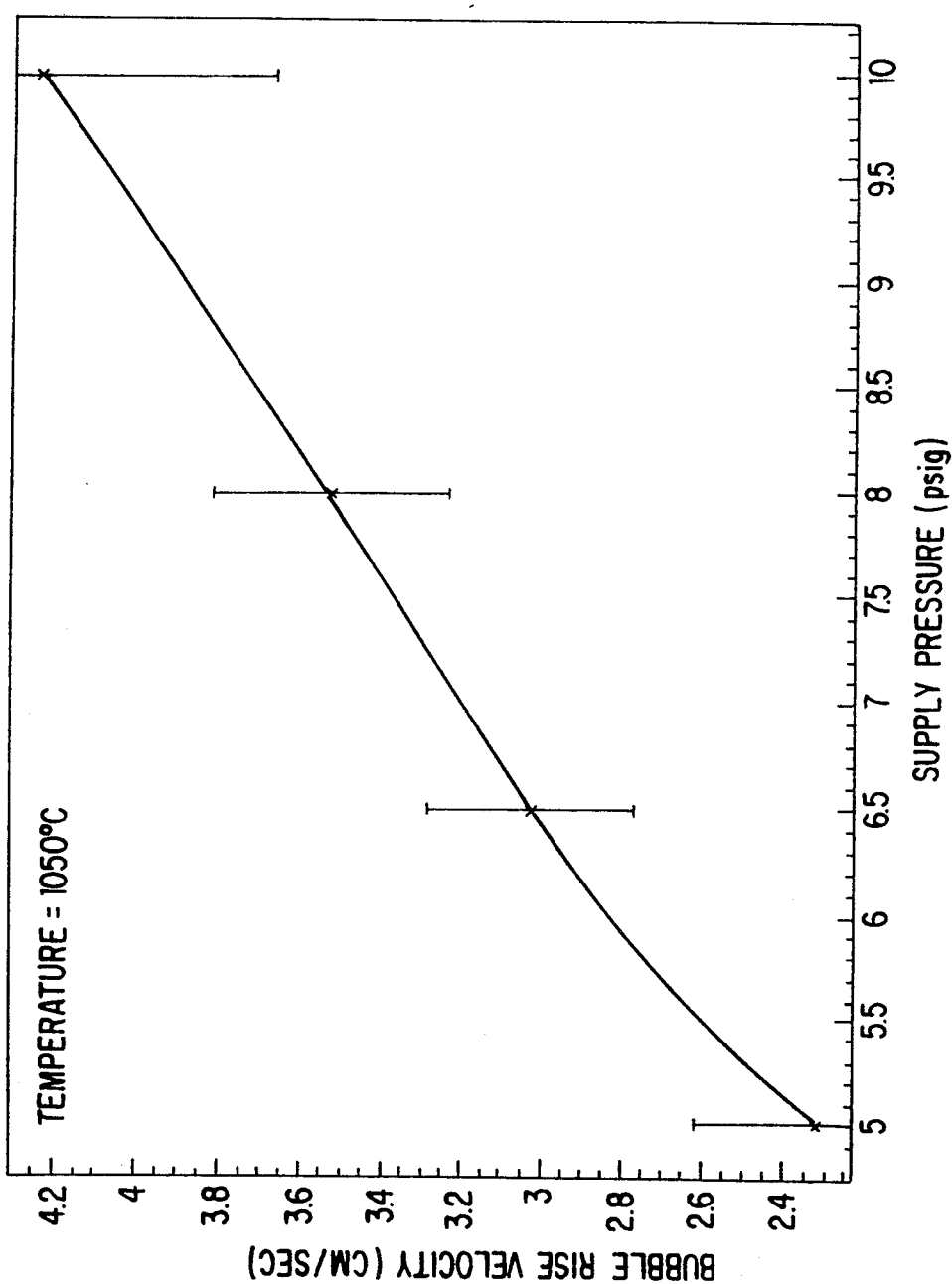
FIG. 8 shows the BRV as a function of supply pressure for Savannah River Laboratory waste glass.

Experimental data for the BRVs for Savannah River Laboratory waste glass as a function of temperature and supply pressure are shown in FIGS. 7 and 8. This type of data can be used for the development of empirical equations for the conversion of BRV data to dynamic viscosities.

Figure 9:
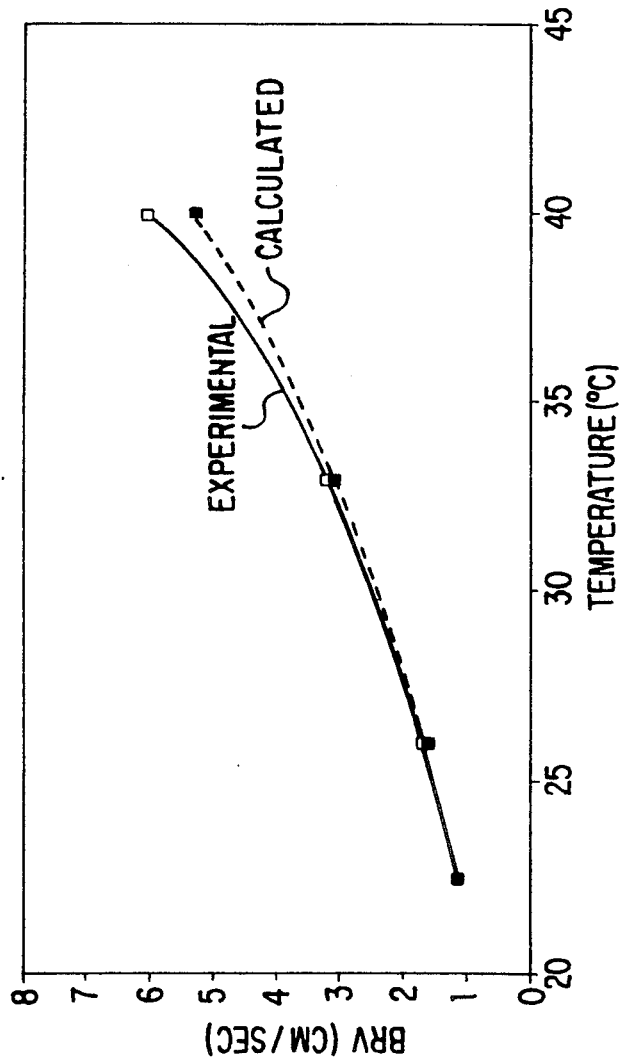
FIG. 9 shows a plot of experimental and calculated BRVs for S-2000 Oil as a function of temperature.

FIG. 9 shows experimental BRVs obtained using the apparatus of this invention for S-2000 oil and BRVs calculated using the Hadamard-Rybczynski (H-R) formula at several temperatures. There appears to be a systematic bias between the two sets, suggesting that a modification of the H-R formula would be necessary.

Figure 10:
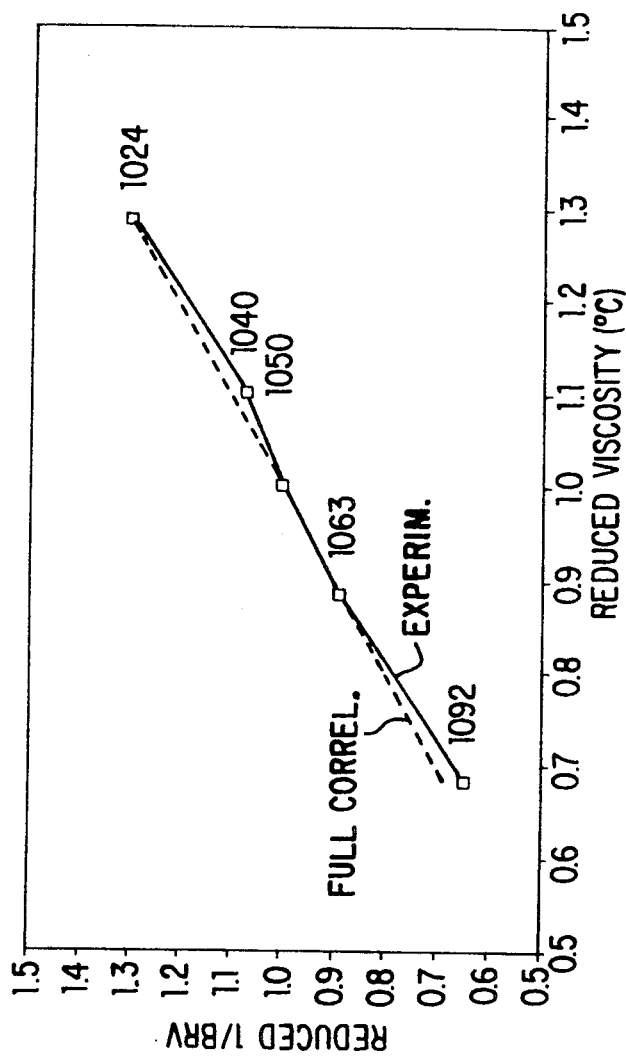
FIG. 10 shows a comparison of reduced reciprocal BRVs and reduced viscosities for Savannah River Laboratory waste glass.

To test the overall utility of the BRV method used in an entirely remotely operated mode, a reduced properties plot, as described above, was prepared for Savannah River Laboratory waste glass. As is shown in FIG. 10, there is excellent agreement between the BRVs and the viscosities reported for Savannah River Laboratory waste glass.

What is claimed is:

1. An apparatus for determining a first composition-dependent physical property of a fluid, comprising:
   a) a container for holding the fluid at a certain level in order to form a surface on the fluid;
   b) means for introducing into the fluid at a first depth a first bubble having a first size;
   c) means for generating a carrier gas stream;
   d) means for capturing in the carrier gas stream the first bubble as it leaves the surface of the fluid; and
   e) means in the path of travel of the carrier gas stream to detect the first bubble in order to determine the time of transit of the bubble from first depth to the surface of the fluid, so as to enable calculation of the average bubble rise velocity.

2. The apparatus of claim 1, wherein the bubble is formed by a gas.

3. The apparatus of claim 2, wherein the first bubble introducing means comprises:
   a) a first bubble delivery tube having a first end connected to a source of gas which forms the first bubble and a second end for delivering the bubble into the fluid;
   b) a metering chamber intermediate the source and the second end and in flow communication therewith;
   c) a first valve intermediate the second end and the metering chamber to regulate the flow of the gas from the metering chamber to the second end of the delivery tube;
   d) a second valve intermediate the source and the metering chamber to regulate the flow of the gas flowing into the metering chamber; and
   e) means for opening and closing the valves sequentially to deliver a known mass of the gas in a pulsatile fashion to the second end of the delivery tube to form the first bubble.

4. The apparatus of claim 3, wherein the valves are fast-acting solenoid valves.

5. The apparatus of claim 3, and further comprising means for sensing the gas pressure in the first bubble delivery tube before and after the first valve is opened to determine the mass of the gas in the bubble.

6. The apparatus of claim 5, wherein the gas pressure sensing means allows detection of the gas pressure in the first bubble delivery tube after the first valve is opened to determine the time the bubble is introduced into the fluid from the first depth.

7. The apparatus of claim 3, further comprising means for sensing the gas pressure at a plurality of depths of the fluid to determine the density of the fluid.

8. The apparatus of claim 3, wherein the first bubble delivery tube comprises a U-tube.

9. The apparatus of claim 3, wherein the first bubble delivery tube comprises an L-shaped tube.

10. The apparatus of claim 1, wherein the bubble is formed by a liquid immiscible with the fluid.

11. The apparatus of claim 1, further comprising means for controlling the determination of the first composition-dependent physical property from a location remote to the container holding the fluid.

12. The apparatus of claim 1, further comprising means for introducing into the fluid at a second depth a second bubble having a second size, wherein the second bubble introducing means is positioned so that the second bubble is captured in the carrier gas stream as the second bubble leaves the surface of the fluid.

13. The apparatus of claim 12, wherein the second bubble introducing means comprises:
   a) a second bubble delivery tube having a first end connected to a source of gas which forms the second bubble and a second end for delivering the bubble into the fluid;
   b) a metering chamber intermediate the source and the second end and in flow communication therewith;
   c) a first valve intermediate the second end and the metering chamber to regulate the flow of the gas from the metering chamber to the second end of the second bubble delivery tube;
   d) a second valve intermediate the source and the metering chamber to regulate the flow of the gas flowing into the metering chamber; and
   e) means for opening and closing the valves sequentially to deliver a known mass of the gas in a pulsatile fashion to the second end of the second bubble delivery tube to form the second bubble.

14. The apparatus of claim 13, further comprising means to detect the gas pressure at the first and second depths to allow measurement of the differential hydrostatic pressure between the first and second depths.

15. The apparatus of claim 1, wherein the bubble detecting means is a helium detector.

16. The apparatus of claim 12, wherein the first bubble and second bubble have approximately equal sizes.

17. The apparatus of claim 1, wherein the means for capturing the gas bubble comprises a hood positioned above the surface of the fluid and further comprising:
 a) a vacuum pump for creating the carrier gas stream, wherein the bubble detecting means is positioned between the pump and the hood along the path of travel of the carrier gas stream; and
 b) means for maintaining the carrier gas stream at a constant velocity, wherein the means for maintaining constant velocity is positioned between the pump and the bubble detecting means along the path of travel of the carrier gas stream.

18. The apparatus of claim 1, wherein the bubble detecting means is a differential thermal conductivity cell.

19. The apparatus of claim 1, wherein the bubble detecting means comprise a mass spectrometer type leak detector.

20. The apparatus of claim 1, and further comprising means for determining the density of the fluid to enable calculation of the dynamic viscosity of the fluid.

21. The apparatus of claim 1, and further comprising:
 a) means for monitoring a second composition-dependent physical property of the fluid; and
 b) means for sensing the temperature of said fluid, to enable determination of the composition of the fluid.

22. The apparatus of claim 21, wherein the second composition-dependent physical property is density.

23. The apparatus of claim 21, wherein the second composition-dependent physical property is electrical resistivity.

24. The apparatus of claim 21, and further comprising means for controlling the determination of the second composition-dependent physical property from a location remote to the container holding the fluid.

25. A method of monitoring a first composition-dependent physical property of a fluid, comprising the steps of:
 a) introducing into the fluid at a first depth a first bubble having a first size;
 b) capturing in a carrier gas stream the first bubble as it leaves the surface of the fluid; and
 c) detecting the presence of the first bubble in the carrier gas stream in order to determine the time of transit of the bubble from the first depth to the surface of the fluid to allow calculation of the average bubble rise velocity.

26. The method of claim 25, wherein the first composition-dependent physical property is monitored from a location remote to the container holding the fluid.

27. The method of claim 25, and further comprising the step of introducing into the fluid at a second depth a second bubble having a second size, wherein the first bubble and the second bubble will rise to the surface of the fluid at different times to allow calculation of the average bubble rise velocity between the first and second depth.

28. The method of claim 25, and further comprising the step of determining the density of the fluid to enable calculation of the dynamic viscosity of the fluid.

29. The method of claim 25, wherein the fluid comprises a ternary system, and further comprising the steps of:
 a) monitoring a second composition-dependent physical property of the fluid;
 b) monitoring the temperature of the fluid;
 c) preparing a triangular phase diagram for the fluid; and
 d) determining the composition of the fluid by locating the point where the isopleths of the viscosity and the second composition-dependent physical property intersect on the triangular phase diagram for the fluid, in order to monitor the composition of the fluid.

30. The method of claim 29, wherein the composition of the fluid is monitored from a location remote to the container holding the fluid.

31. The method of claim 29, wherein the second composition-dependent physical property is density.

32. The method of claim 29, wherein the second composition-dependent physical property is electrical resistivity.

33. The method of claim 25, wherein the fluid comprises a molten glass.

34. The method of claim 33, wherein the glass comprises radioactive waste glass.

35. The method of claim 25, wherein the monitoring of the fluid is continuous or near-continuous.

* * * * *